US011638793B2

(12) United States Patent
Dubief et al.

(10) Patent No.: US 11,638,793 B2
(45) Date of Patent: *May 2, 2023

(54) AEROSOL GENERATING DEVICE HAVING AN INTERNAL HEATER

(71) Applicant: Philip Morris Products S.A., Neuchatel (CH)

(72) Inventors: Flavien Dubief, Neuchatel (CH); Olivier Cochand, Dombresson (CH); Michel Thorens, Moudon (CH); Jean-Marc Flick, Pomy (CH); Yvan Degoumois, Colombier (CH)

(73) Assignee: Philip Morris Products S.A., Neuchatel (CH)

( * ) Notice: Subject to any disclaimer, the term of this patent is extended or adjusted under 35 U.S.C. 154(b) by 205 days.

This patent is subject to a terminal disclaimer.

(21) Appl. No.: 16/952,415

(22) Filed: Nov. 19, 2020

(65) Prior Publication Data

US 2021/0076739 A1     Mar. 18, 2021

Related U.S. Application Data

(63) Continuation of application No. 16/171,014, filed on Oct. 25, 2018, now Pat. No. 10,881,149, which is a
(Continued)

(30) Foreign Application Priority Data

Dec. 8, 2011 (EP) ..................... 11192696

(51) Int. Cl.
*A24F 40/46* (2020.01)
*A61M 11/04* (2006.01)
(Continued)

(52) U.S. Cl.
CPC ............. *A61M 15/06* (2013.01); *A24F 40/42* (2020.01); *A24F 40/46* (2020.01); *A61M 11/041* (2013.01);
(Continued)

(58) Field of Classification Search
None
See application file for complete search history.

(56) References Cited

U.S. PATENT DOCUMENTS

| 4,945,929 A | 8/1990 | Egilmex |
| 5,144,962 A | 9/1992 | Counts et al. |

(Continued)

FOREIGN PATENT DOCUMENTS

| AT | 3894389 A | 2/1990 |
| CA | 02 752 255 A1 | 8/2010 |

(Continued)

OTHER PUBLICATIONS

Machine translation of CN20175712, European Patent Office and Google, [online], retrieved from the Internet, [retrieved Jul. 29, 2017], <URL: https://worldwide.espacenet.com/?locale=EN_ep>. (Year: 2017).*

(Continued)

*Primary Examiner* — Dennis R Cordray
(74) *Attorney, Agent, or Firm* — Oblon, McClelland, Maier & Neustadt, L.L.P.

(57) ABSTRACT

An aerosol generating device is provided, including a storage portion to store an aerosol-forming substrate and having an outer housing and an internal passageway, the portion forming a reservoir for the substrate between the housing and the passageway; a vaporizer including an electric heater to heat the substrate to form an aerosol, the vaporizer at least partially inside the passageway; and a porous interface at least partially lining the passageway to convey the substrate (Continued)

towards the vaporizer, the device being electrically operated, the heater including first and second electrical connection portions, and a heating filament therebetween, a cylindrical shape of the connection portions and the filament define a cylindrical bore, an air flow route is defined through the bore, and the first connection portion being a first cylindrical electrical connection portion, the second connection portion being a second cylindrical electrical connection portion, and the filament being a cylindrical heating element.

19 Claims, 2 Drawing Sheets

Related U.S. Application Data continuation of application No. 14/363,531, filed as application No. PCT/EP2012/074510 on Dec. 5, 2012, now Pat. No. 10,143,233.

(51) Int. Cl.
*A61M 15/06* (2006.01)
*A61M 16/00* (2006.01)
*A24F 40/42* (2020.01)
*A24F 40/10* (2020.01)

(52) U.S. Cl.
CPC ............ *A61M 11/042* (2014.02); *A24F 40/10* (2020.01); *A61M 2016/0015* (2013.01); *A61M 2205/8206* (2013.01); *A61M 2205/8268* (2013.01)

(56) References Cited

U.S. PATENT DOCUMENTS

| | | |
|---|---|---|
| 8,689,805 B2 | 4/2014 | Hon |
| 2009/0095311 A1 | 4/2009 | Han |
| 2009/0126745 A1 | 5/2009 | Hon |
| 2009/0261046 A1 | 10/2009 | Minnie et al. |
| 2009/0302019 A1 | 12/2009 | Selenski et al. |
| 2011/0155718 A1 | 6/2011 | Greim et al. |
| 2011/0209717 A1 | 9/2011 | Han |

FOREIGN PATENT DOCUMENTS

| | | | |
|---|---|---|---|
| CA | 2 884 987 A1 | | 8/2010 |
| CN | 1190335 A | | 8/1998 |
| CN | 1209731 A | | 3/1999 |
| CN | 1252961 A | | 5/2000 |
| CN | 1575673 A | | 2/2005 |
| CN | 2719043 Y | | 8/2005 |
| CN | 101084034 A | | 12/2007 |
| CN | 101277623 A | | 10/2008 |
| CN | 101341028 A | | 1/2009 |
| CN | 101483941 A | | 7/2009 |
| CN | 101843368 A | | 9/2010 |
| CN | 101878958 A | | 11/2010 |
| CN | 201623865 U | | 11/2010 |
| CN | 201691064 U | | 1/2011 |
| CN | 201733471 U | | 2/2011 |
| CN | 201750712 U | * | 2/2011 |
| CN | 101986906 A | | 3/2011 |
| CN | 102014677 A | | 4/2011 |
| CN | 102052541 A | | 5/2011 |
| EA | 004280 B1 | | 2/2004 |
| EP | 0 430 559 | | 6/1991 |
| EP | 2 022 349 | | 2/2009 |
| EP | 2 316 286 | | 5/2011 |
| EP | 2 340 730 | | 7/2011 |
| EP | 2 787 846 B1 | | 3/2016 |
| GB | 2469850 | | 11/2010 |
| JP | 60-9189 U | | 1/1985 |
| JP | 62-117288 A | | 5/1987 |
| JP | 3-232481 A | | 10/1991 |
| JP | 2011-518567 A | | 6/2011 |
| KR | 0178388 B1 | | 11/1998 |
| KR | 10-1999-0007914 A | | 1/1999 |
| KR | 10-0340825 B1 | | 6/2002 |
| RU | 110 607 U1 | | 11/2011 |
| WO | WO 02/03819 A1 | | 1/2002 |
| WO | WO 2007/066374 A1 | | 6/2007 |
| WO | WO 2008/087161 A1 | | 7/2008 |
| WO | WO 2009/132793 A1 | | 11/2009 |
| WO | WO 2010/091593 A1 | | 8/2010 |
| WO | WO 2011/079932 A1 | | 7/2011 |
| WO | 2011 146174 | | 11/2011 |
| WO | WO 2013/083631 A1 | | 6/2013 |

OTHER PUBLICATIONS

Definition of bore, Merriam-Webster Dictionary, no date [online],retrieved from the Internet,[retrieved Aug. 6, 202, <URL:https://www.merriam-webster.com/dictionary/bore>. (Year: 2022).*
International Search Report dated Mar. 22, 2013 in PCT/EP12/074510 Filed Dec. 5, 2012.
Written Opinion of the International Searching Authority dated Mar. 22, 2013 in PCT/EP12/074510 Filed Dec. 5, 2012.
Examination Report dated Feb. 29, 2016 in GCC Patent Application No. GC 2012-22990.
Machine translation of CN201750712, European Patent Office and Google, [online], retrieved from the Internet, [retrieved Jul. 29, 2017], <URL:https://worlwide.espacenet.com/?locale=EN_ep.>.
Office Action dated Aug. 20, 2015 in Kazak Patent Application No. 2014/1631.1 (with English language translation).
Combined Chinese Office Action and Search Report dated Oct. 29, 2015 in Patent Application No. 201280060089.X (with English language translation).
Third Party Observations dated Feb. 3, 2016 in Japanese Patent Application No. 2014-545241.
Office Action dated Oct. 3, 2016 in Japanese Patent Application No. 2014-545241 (with English language translation).
Notice of Opposition dated Dec. 21, 2016 in European Patent Application No. 12812186.0, Patent No. 2787846.
Extended European Search Report dated May 14, 2014 in the corresponding European Application No. 11192696.0.
International Preliminary Report on Patentability and Written Opinion dated Jun. 10, 2014 in PCT/EP2012/074510.
Office Action dated Jun. 9, 2016 in Russian Patent Application No. 2014127682 (with English language translation).
Office Action dated Nov. 15, 2018 in Korean Patent Application No. 2014-7013501, 11 pages (with English language translation).
Japanese Decision of Final Rejection dated Mar. 18, 2019 in Japanese Patent Application No. 2017-134326 (with English translation), 7 pages.
Office Action dated Sep. 20, 2019 in Korean Patent Application No. 10-2014-7013501, 6 pages (with English translation).
Definition of "diameter", Merriam-Webster Dictionary, [online], retrieved from the Internet, [Jun. 13, 2010], <URL:https// www.merriam-webster.com/dictionary/diameter>. (Year: 2020).
Combined Chinese Office Action and Search Report dated Sep. 17, 2021 in Chinese Patent Application No. 201910004599.9 (with English translation), 15 pages.
Combined Chinese Office Action and Search Report dated Feb. 20, 2021 in Chinese Patent Application No. 201910004599.9 (with English translation), 41 pages.
U.S. Appl. No. 16/171,014, filed Oct. 25, 2018, 2019/0059447 A1, Flavien Dubief, et al.
U.S. Pat. No. 10,143,233, Dec. 4, 2018, 2015/0181937 A1, Flavien Dubief, et al.
Japanese Office Action dated Oct. 29, 2020 in Japanese Patent Application No. 2019-132404 (with English translation), 8 pages.
Combined Chinese Office Action and Search Report dated Jun. 1, 2022 in Chinese Patent Application No. 20190004599.9 (with Translation of Category of Cited Documents), 5 pages.

(56) References Cited

OTHER PUBLICATIONS

Combined Chinese Office Action and Search Report dated Mar. 7, 2022 in Chinese Patent Application No. 201910004599.9 (with English translation), 20 pages.

* cited by examiner

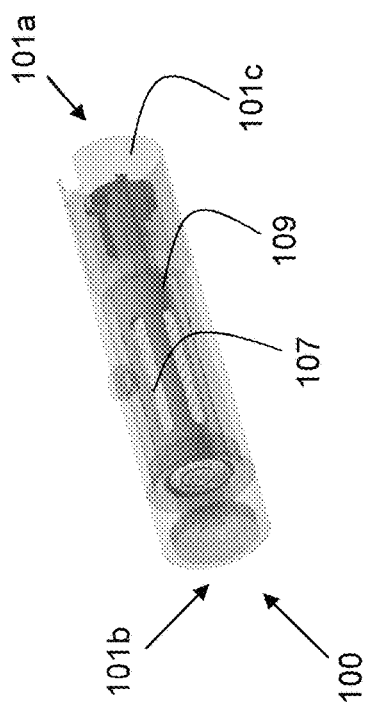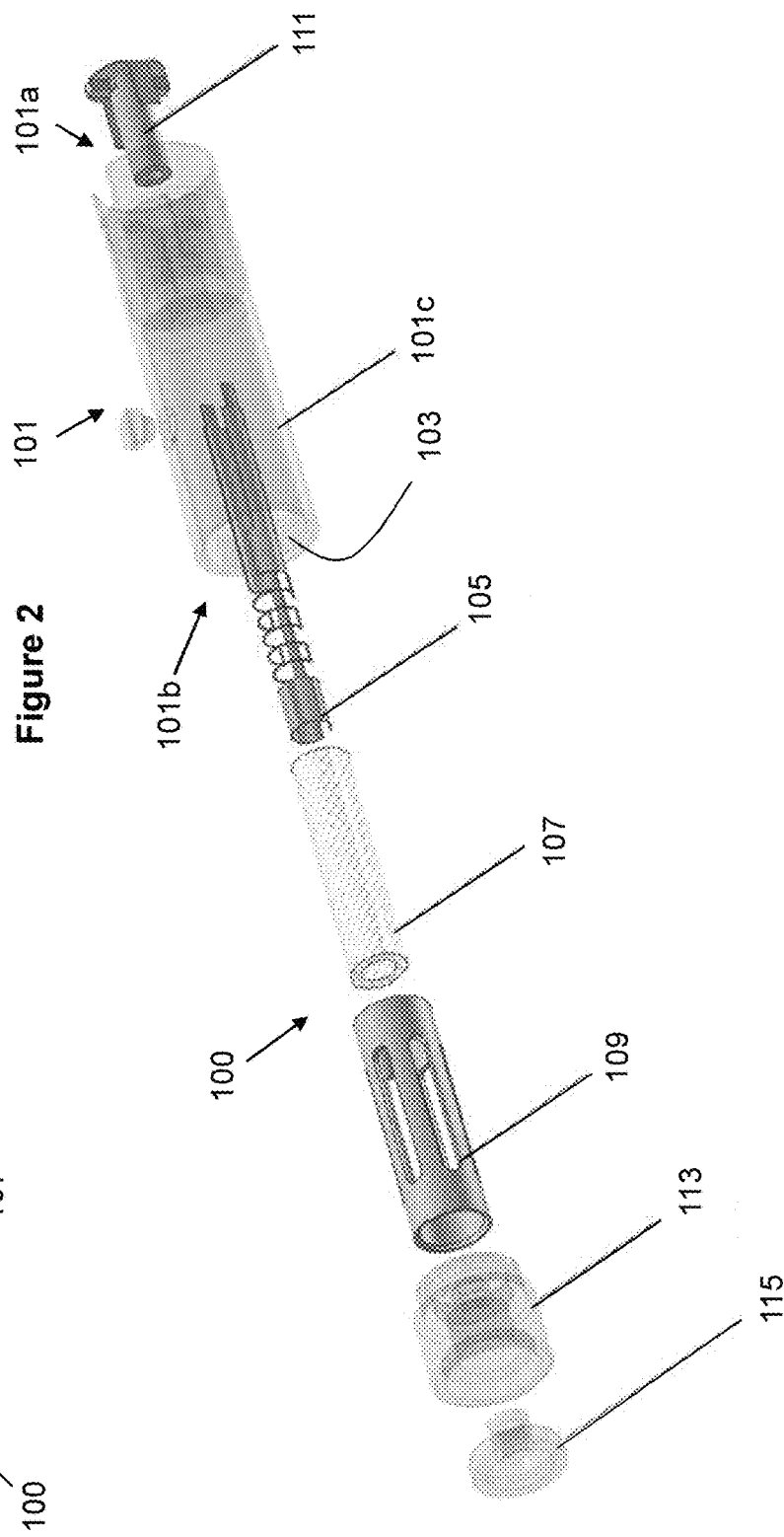

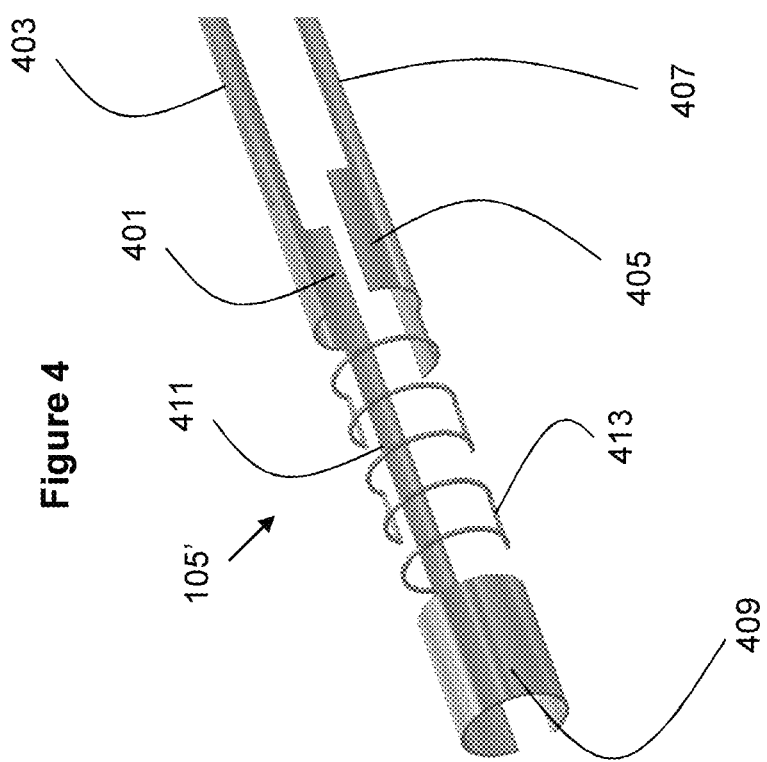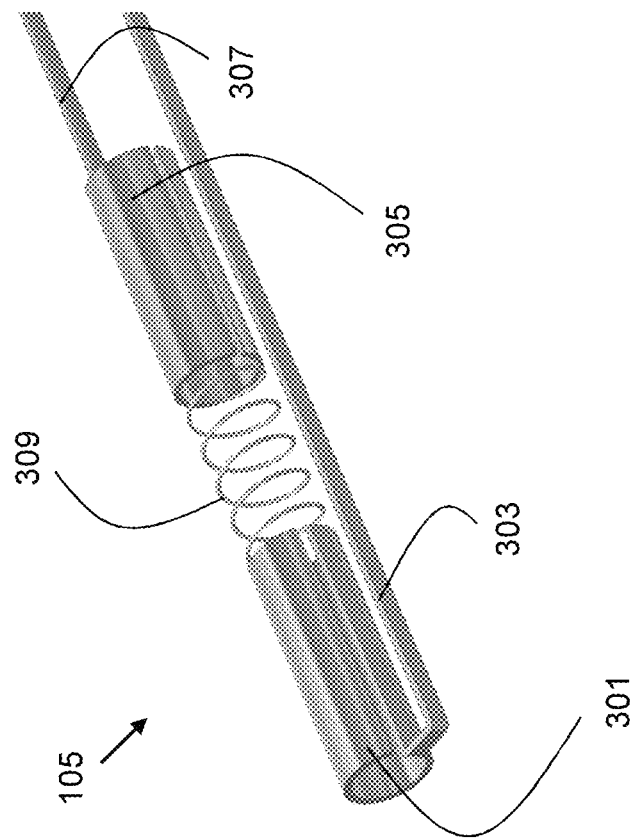

AEROSOL GENERATING DEVICE HAVING AN INTERNAL HEATER

CROSS-REFERENCE TO RELATED APPLICATIONS

This application is a continuation application of and claims the benefit of priority under 35 U.S.C. § 120 to U.S. application Ser. No. 16/171,014, filed Oct. 25, 2018, which is a continuation of U.S. application Ser. No. 14/363,531, filed on Jun. 6, 2014 (now U.S. Pat. No. 10,143,233), which is a U.S. National Stage application of PCT/EP12/74510, filed on Dec. 5, 2012, and claims benefit of priority under 35 U.S.C. § 119 to EP 11192696.0, filed on Dec. 8, 2011, the entire contents of each of which are incorporated herein by reference.

The present invention relates to an aerosol generating device for heating an aerosol-forming substrate. Particularly, but not exclusively, the present invention relates to an electrically operated aerosol generating device for heating a liquid aerosol-forming substrate.

WO-A-2009/132793 discloses an electrically heated smoking device. A liquid is stored in a liquid storage portion, and a capillary wick has a first end which extends into the liquid storage portion for contact with the liquid therein, and a second end which extends out of the liquid storage portion. A heating element heats the second end of the capillary wick. The heating element is in the form of a spirally wound electric heating element in electrical connection with a power supply, and surrounding the second end of the capillary wick. In use, the heating element may be activated by the user to switch on the power supply. Suction on a mouthpiece by the user causes air to be drawn into the electrically heated smoking device over the capillary wick and heating element and subsequently into the mouth of the user.

It is an objective of the present invention to improve the generation of aerosol in an aerosol generating device or system.

According to one aspect of the invention, there is provided an aerosol generating device comprising: a storage portion for storing an aerosol-forming substrate, the storage portion having an outer housing and an internal passageway, the storage portion forming a reservoir for the aerosol-forming substrate between the outer housing and the internal passageway; a vaporizer for heating the aerosol-forming substrate to form an aerosol, the vaporizer at least partially inside the internal passageway in the storage portion; and a porous interface at least partially lining the internal passageway for conveying the aerosol-forming substrate from the storage portion towards the vaporizer.

The aerosol generating device is arranged to vaporize an aerosol-forming substrate to form the aerosol. The aerosol generating device may include the aerosol-forming substrate or may be adapted to receive the aerosol-forming substrate. As known to those skilled in the art, an aerosol is a suspension of solid particles or liquid droplets in a gas, such as air.

According to another aspect of the invention, there is provided a cartridge comprising: a storage portion for storing an aerosol-forming substrate, the storage portion having an outer housing and an internal passageway, the storage portion forming a reservoir for the aerosol-forming substrate between the outer housing and the internal passageway; a vaporizer for heating the aerosol-forming substrate to form an aerosol, the vaporizer at least partially inside the internal passageway in the storage portion; and a porous interface at least partially lining the internal passageway for conveying the aerosol-forming substrate from the storage portion towards the vaporizer.

The aerosol generating device and cartridge may cooperate to provide an aerosol generating system for heating the aerosol-forming substrate. The cartridge or aerosol generating device may comprise the storage portion having the internal passageway. The vaporizer and the porous interface may be contained in the aerosol generating device. The vaporizer and the porous interface may also be contained in the cartridge.

The aerosol generating device may comprise the vaporizer for heating the aerosol-forming substrate. Alternatively or additionally, the aerosol generating device may comprise the porous interface. The aerosol generating device may comprise the storage portion for storing the aerosol forming substrate.

The cartridge may comprise the vaporizer for heating the aerosol-forming substrate. Alternatively or additionally, the cartridge may comprise the porous interface. The cartridge may comprise the storage portion for storing the aerosol forming substrate.

According to another aspect of the invention, there is provided an aerosol generating system comprising: a cartridge and an aerosol generating device, the cartridge or the aerosol generating device comprising: a storage portion for storing an aerosol-forming substrate, the storage portion having an internal passageway; a vaporizer for heating the aerosol-forming substrate to form an aerosol, the vaporizer at least partially inside the internal passageway in the storage portion; and a porous interface at least partially lining the internal passageway for conveying the aerosol-forming substrate from the storage portion towards the vaporizer.

For all aspects of the invention, the storage portion may be a liquid storage portion. For all aspects of the invention, the aerosol forming substrate may be a liquid aerosol forming substrate. The aerosol-forming substrate may contain nicotine. The aerosol-forming substrate may be adsorbed, coated, impregnated or otherwise loaded onto a carrier or support.

The aerosol-forming substrate may alternatively be any other sort of substrate, for example, a gas substrate or a gel substrate, or any combination of the various types of substrate. The aerosol-forming substrate may be a solid substrate.

The porous interface may be arranged to be in contact with liquid aerosol-forming substrate in the liquid storage portion. In one embodiment, liquid aerosol-forming substrate in the porous interface is vaporized by the heater to form a supersaturated vapour. The supersaturated vapour is mixed with air. The supersaturated vapour condenses to form the aerosol and the aerosol is carried towards the mouth of a user. The liquid aerosol-forming substrate has suitable physical properties, including surface tension and viscosity, which allow the liquid to be transported through the porous interface.

In this invention, the vaporizer at least partially extends inside the internal passageway of the storage portion. By having the vaporizer at least partially inside the internal passageway, a number of advantages can be found. First, manufacture and assembly of the aerosol generating device and cartridge is easier and faster because of the simplified design of the parts. Second, because the vaporizer extends at least partially inside the internal passageway of the storage portion rather than downstream of the storage portion, the length of the aerosol generating device and the cartridge can be optionally reduced. Third, because the vaporizer extends at least partially inside the internal passageway of the storage portion, the vaporizer may be protected from damage, bending, or distortion. Fourth, the storage portion may act as an insulator which, if the vaporizer comprises a heater, may prevent the housing of the aerosol generating device from overheating. Fifth, because the porous interface at least partially lines the internal passageway, gravity may assist in conveying liquid from the storage portion and this reduces the chance of the porous interface drying out. Finally, any aerosol which condenses after formation may be used again by the porous interface, thereby reducing wastage and leakage.

The storage portion may protect the aerosol-forming substrate from ambient air (because air cannot generally enter the storage portion). The storage portion may protect the aerosol-forming substrate from light, so that the risk of degradation of the aerosol-forming substrate is significantly reduced. Moreover, a high level of hygiene can be maintained. The storage portion may not be refillable. Thus, when the aerosol-forming substrate in the storage portion has been used up, the aerosol generating device or cartridge is replaced. Alternatively, the storage portion may be refillable. In that case, the aerosol generating device or cartridge may be replaced after a certain number of refills of the storage portion. The storage portion may be arranged to hold aerosol-forming substrate for a pre-determined number of puffs. Therefore, the volume of the storage portion may be expanded or contracted based on the number of desirable puffs.

In one embodiment, the storage portion comprises a container. Preferably, the container has a constant cross sectional shape and size along its length. The storage portion preferably has an outer dimension defining the exterior of the storage portion. The outer dimension may be substantially equal to the dimension of the aerosol generating device, thereby allowing the storage portion to cooperate effectively with the aerosol generating device. Preferably, the internal passageway has a constant cross sectional shape and size along its length. Preferably, the internal passageway is aligned with the longitudinal axis of the storage portion. That is to say, preferably the internal passageway is a central passageway. Alternatively, the internal passageway may not be aligned with the longitudinal axis of the storage portion. That is to say, the internal passageway may be off-centre. The storage portion preferably has an inner dimension defining the dimension of the internal passageway.

In a preferred embodiment, the storage portion comprises a prism-shaped container having an annular cross section, wherein the inner radius of the annulus is the radius of the internal passageway of the container, and the outer radius of the annulus defines the exterior of the container.

Preferably, in use, liquid is transferred from the storage portion to the vaporizer through the porous interface. The construction of the vaporizer may enable it to be usable with a variety of different shapes and sizes of storage portion. The inner side of the porous interface could be in contact with the liquid in the storage portion. The outer side of the porous interface could be in contact with or adjacent the vaporizer. In one embodiment, liquid in the outer side of the porous interface is vaporized to form the supersaturated vapour. The liquid aerosol-forming substrate has suitable physical properties, including surface tension and viscosity, which allow the liquid to be transported through the porous interface.

The porous interface may comprise any suitable material or combination of materials which is able to convey the aerosol-forming substrate towards the vaporizer. The porous interface may comprise a capillary material, but this need not be the case. The porous interface may have a fibrous or spongy structure. The porous interface may comprise a bundle of capillaries. For example, the porous interface may comprise a plurality of fibres or threads or other fine bore tubes. Alternatively, the porous interface may comprise sponge-like or foam-like material. The structure of the porous interface may form a plurality of small bores or tubes, through which the aerosol-forming substrate can be transported by capillary action from the storage portion towards the vaporizer. The particular preferred porous material or materials will depend on the suitable physical properties of the aerosol-forming substrate. Examples of suitable porous materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The porous interface may have any suitable porosity so as to be used with different liquids. The liquid has suitable physical properties and certain parameters need to be taken into account, including, but not limited to, viscosity, surface tension, density, thermal conductivity, boiling point and vapour pressure, which allow the liquid to be transported through the porous interface.

The porous interface may have any suitable shape for cooperation with the storage portion. Preferably, the porous interface has the same shape and dimension as the internal passageway, thereby allowing the porous interface to fit snugly in the internal passageway. Preferably, the porous interface fully lines the internal passageway. However, the porous interface may only partially line the internal passageway.

In a preferred embodiment, in which the storage portion comprises a container in the shape of a prism having an annular cross section. Preferably the porous interface comprises a hollow tube of porous material, the outer dimension of the hollow tube being substantially equal to the diameter of the internal passageway of the storage portion. The tube of porous material may extend along all of or part of the length of the internal passageway in the storage portion.

The vaporiser may be a heater. The heater may heat the aerosol-forming substrate means by one or more of conduction, convection and radiation. The heater may be an electric heater powered by an electric power supply. The heater may alternatively be powered by a non-electric power supply, such as a combustible fuel: for example, the heater may comprise a thermally conductive element that is heated by combustion of a gas fuel. The heater may heat the aerosol-forming substrate by means of conduction and may be at least partially in contact with the substrate, or a carrier on which the substrate is deposited. Alternatively, the heat from the heater may be conducted to the substrate by means of an intermediate heat conductive element. Alternatively, the heater may transfer heat to the incoming ambient air that is drawn through the aerosol-generating system during use, which in turn heats the aerosol-forming substrate by convection.

In a preferred embodiment, the aerosol generating device is electrically operated and the vaporizer of the aerosol generating device comprises an electric heater for heating the aerosol-forming substrate.

The electric heater may comprise a single heating element. Alternatively, the electric heater may comprise more than one heating element for example two, or three, or four, or five, or six or more heating elements. The heating element or heating elements may be arranged appropriately so as to most effectively heat the aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium- titanium-, zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one electric heating element may comprise an infra-red heating element, a photonic source or an inductive heating element.

The at least one electric heating element may take any suitable form. For example, the at least one electric heating element may take the form of a heating blade or heating needles or rods. Alternatively, the at least one electric heating element may take the form of a casing or substrate having different electro-conductive portions, or an electrically resistive metallic tube. The liquid storage portion may incorporate a disposable heating element. The at least one electric heating element may comprise a flexible sheet of material. Other alternatives include a heating wire or filament, for example a Ni—Cr (nickel-chromium), platinum, tungsten or alloy wire, or a heating plate. Optionally, the heating element may be deposited in or on a rigid carrier material.

The at least one electric heating element may comprise a heat sink, or heat reservoir, comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material. Other suitable materials which release heat via a reversible phase change include paraffin, sodium acetate, naphthalene, wax, polyethylene oxide, a metal, metal salt, a mixture of eutectic salts or an alloy.

The heat sink may be arranged such that it is directly in contact with the aerosol-forming substrate in the porous interface and can transfer the stored heat directly to the aerosol-forming substrate. Alternatively, the heat stored in the heat sink or heat reservoir may be transferred to the aerosol-forming substrate in the porous interface by means of a heat conductor, such as a metallic tube.

The at least one heating element may heat the aerosol-forming substrate by means of conduction. The heating element may be at least partially in contact with the aerosol-forming substrate. Alternatively, the heat from the heating element may be conducted to the aerosol-forming substrate by means of a heat conductor.

Alternatively or in addition, the at least one heating element may transfer heat to the incoming ambient air that is drawn through the aerosol generating device during use, which in turn heats the aerosol-forming substrate by convection. The ambient air may be heated before passing through the aerosol-forming substrate. Alternatively, the ambient air may be first drawn through the aerosol-forming substrate and then heated.

In one preferred embodiment in which the vaporizer comprises an electric heater, the electric heater comprises: a first electrical connection portion; a second electrical connection portion; and a heating filament between the first and second electrical connection portions.

In one embodiment, when the device is in use with the cartridge the first electrical connection portion is located at a first end of the internal passageway, the second electrical connection portion is located at a second end of the internal passageway, and the heating filament has a first end joined to the first electrical connection portion and a second end joined to the second electrical connection portion. In this embodiment, the first electrical connection portion, the second connection portion and the heating filament are manufactured separately and are then connected together, for example by welding. The heating filament may comprise a heating coil between the first and second electrical connection portions. Other shapes for the heating filament are also possible.

All portions of the heating filament may have the same cross sectional shape and area. Alternatively, some portions of the heating filament may have a different cross sectional shape or area from other portions of the heating filament.

In an alternative embodiment, the electric heater comprises a sheet of electrically resistive material shaped to form the first electrical connection portion, the second electrical connection portion and the heating filament. In this embodiment, the first electrical connection portion, the second electrical connection portion and the heating filament are integrally formed from the sheet of electrically resistive material. The term "integrally formed" refers to the first electrical connection portion, the second electrical connection portion and the heating filament being manufactured as one single part from a single piece of material. Providing an integrally formed electric heater simplifies manufacture of the heater.

The sheet of electrically resistive material may have any suitable shape. The heating filament, first electrical connection portion and second electrical connection portion may be formed by shaping from the sheet of electrically resistive material. For example, the heating filament may be cut from the sheet of electrically resistive material, for example, by a laser or by a chemical or electrical processor by high pressure water jet. Alternatively, the heating filament may be pre-formed in the desired shape.

The sheet of electrically resistive material may be a flexible sheet of material. Preferably, the flexible sheet of material is folded, rolled, curved or bent so as to form the electric heater, which is correctly shaped to extend through the internal passageway of the liquid storage portion. The sheet of electrically resistive material may have any suitable flexibility.

The heating filament may have the shape of a square wave extending between the electrical connection portions. That is to say, the heating filament may comprise portions extending substantially parallel to the longitudinal axis of the internal passageway and portions extending substantially perpendicular to the longitudinal axis of the internal passageway. The number and size of the portions extending substantially parallel to the longitudinal axis of the internal passageway may be varied. The number and size of the portions extending substantially perpendicular to the longitudinal axis of the internal passageway may be varied. This will affect the ultimate flexibility of the heating element. Alternatively, the heating filament may have any other suitable shape.

All portions of the heating filament may have the same cross sectional shape and area. Alternatively, some portions of the heating filament may have a different cross sectional shape or area from other portions of the heating filament.

In one preferred embodiment, when the device is in use with the cartridge the electric heater at least partially inside the internal passageway is in contact with the porous interface. This improves the heat transfer from the electric heater to the aerosol-forming substrate in the porous interface.

Preferably, the electric heater is elastic. The electric heater may have any suitable elasticity. The elasticity may provide the contact between the electric heater and the porous interface. For example, if the electric heater comprises a sheet of electrically resistive material shaped to form the first and second electrical contact portions and the heating filament, preferably, the folding of the sheet of electrically resistive material results in a spring effect when the electric heater is assembled. This ensures good contact with the porous interface when the electric heater is inside the internal passageway. This ensures a consistent and repeatable smoking experience. In addition, this reduces the likelihood that the electric heater will become dislodged from the internal passageway.

Various shapes for the electric heater have been disclosed, but the skilled person will appreciate that any suitable shape may be used. In addition, the heating filament need not have the same shape extending all the way between the first and second electrical connection portions.

In one preferred embodiment, the aerosol generating device is electrically operated, the vaporizer comprises an electric heater, the liquid storage portion comprises a prism-shaped container, and the porous interface comprises a hollow tube of porous material, having an inner face in contact with liquid in the liquid storage portion and an outer face opposite the inner face, the electric heater being arranged to heat the liquid aerosol-forming substrate near the outer face of the porous interface. Preferably, the electric heater comprises a heating filament in contact with the outer face of the porous interface. In this embodiment, in use, liquid is transferred from the liquid storage portion through the porous interface lining the internal passageway. When the heater is activated, the liquid near the outer face of the porous interface is vaporized by the heater to form the supersaturated vapour. The supersaturated vapour is mixed with and carried in the air flow through the internal passageway in the liquid storage portion. During the flow, the vapour condenses to form the aerosol and the aerosol is carried towards the mouth of a user.

However, the invention is not limited to electric heater vaporizers but may be used in aerosol generating devices and systems in which the vapour and resulting aerosol is generated by a mechanical vaporizer, for example but not limited to a piezo vaporizer or an atomizer using pressurized liquid.

The storage portion and the porous interface, and optionally the vaporizer, may be removable from the aerosol generating device as a single component.

The aerosol generating device or cartridge may comprise at least one air inlet. The aerosol generating device or cartridge may comprise at least one air outlet. In a preferred embodiment, the aerosol generating device or cartridge further comprises at least one air inlet and at least one air outlet, the air inlet and air outlet being arranged so as to define an air flow route from the air inlet to the air outlet via the internal passageway of the storage portion.

Thus, the internal passageway may additionally act as an aerosol-forming chamber for assisting or facilitating generation of the aerosol. One or more additional aerosol-forming chambers may be provided. The aerosol is carried in the air flow route through the internal passageway so as to convey the aerosol to the air outlet and into the mouth of a user. In addition, the size of the internal passageway may be used to assist with control of the aerosol. In particular, a small internal passageway may result in a high air flow rate through the aerosol generating device or cartridge which may result in smaller droplets in the aerosol. A large internal passageway, on the other hand, may result in a low air flow rate through the aerosol generating device or cartridge which may result in larger droplets. The droplet size in the aerosol may affect the user experience. Preferably, the air flows through the vaporizer which has the same diameter as that of the internal passageway. Preferably the size of the internal passageway, and vaporizer, is pre-set according to the aerosol-forming substrate and the desired aerosol properties. Alternatively, however, the size of the internal passageway, and vaporizer, may be variable by a user.

In one embodiment, there is provided a nozzle arranged to extend into the internal passageway. The nozzle allows the incoming air flow to be directed. For example, the nozzle may allow the incoming air flow to be directed directly onto the vaporizer, directly onto the porous interface, across the surface of the vaporizer, across the surface of the porous interface, or in any other desired direction. This may affect the aerosol formation which may, in turn affect the user experience. In addition, the nozzle may provide an air inlet or inlets having a small cross section, which will increase the air flow speed. This may also affect the aerosol formation by reducing the droplet size in the aerosol.

The aerosol generating device may be electrically operated and may further comprise an electric power supply. The electric power supply may be an AC power source or a DC power source. Preferably, the electric power supply is a battery. The aerosol generating device may further comprise electric circuitry. In one embodiment, the electric circuitry comprises a sensor to detect air flow indicative of a user taking a puff. In that case, preferably, the electric circuitry is arranged to provide an electric current pulse to the vaporizer when the sensor senses a user taking a puff. Preferably, the time-period of the electric current pulse is pre-set, depending on the amount of liquid desired to be vaporized. The electric circuitry is preferably programmable for this purpose. Alternatively, the electric circuitry may comprise a manually operable switch for a user to initiate a puff. The time-period of the electric current pulse is preferably pre-set depending on the amount of liquid desired to be vaporized. The electric circuitry is preferably programmable for this purpose.

The liquid aerosol-forming substrate preferably has suitable physical properties, for example boiling point and vapour pressure, suitable for use in the aerosol generating device or cartridge or system. If the boiling point is too high, it may not be possible to vaporize the liquid but, if the boiling point is too low, the liquid may vaporize too readily. The liquid preferably comprises a tobacco-containing material comprising volatile tobacco flavour compounds which are released from the liquid upon heating. Alternatively, or in addition, the liquid may comprise a non-tobacco material. The liquid may include aqueous solutions, non-aqueous solvents such as ethanol, plant extracts, nicotine, natural or artificial flavours or any combination of these. Preferably, the liquid further comprises an aerosol former that facilitates the formation of a dense and stable aerosol. Examples of suitable aerosol formers are glycerine and propylene glycol.

Preferably, the aerosol generating device or cartridge comprises a housing. Preferably, the housing is elongate. Preferably, the longitudinal axis of the housing is substantially aligned with the longitudinal axis of the internal passageway in the storage portion. The housing may comprise a shell and a mouthpiece. In that case, all the components may be contained in either the shell or the mouthpiece. In one embodiment, the housing includes a removable insert comprising the storage portion, the vaporizer and the porous interface. In that embodiment, those parts of the aerosol generating device may be removable from the housing as a single component. This may be useful for refilling or replacing the storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle. The storage portion may also comprise any suitable material or combination of materials, and may comprise the same or different materials as the housing.

In one particularly preferred embodiment, the cartridge comprises: a mouthpiece; a vaporizer comprising an electric heater for heating the aerosol-forming substrate, the heater being connectable to an electric power supply and electric circuitry in a device; and a storage portion for storing the aerosol forming substrate, wherein the electric heater and a porous interface are arranged in the cartridge.

The storage portion, and optionally the porous interface and the heater, may be removable from the aerosol generating system as a single component. The storage portion, and optionally the porous interface and the heater, may be removable from the aerosol generating system as a cartridge.

Preferably, the aerosol generating device and cartridge are portable, both individually and in cooperation. Preferably, the device is reusable by a user. Preferably, the cartridge is disposable by a user, for example when there is no more liquid contained in the liquid storage portion. The device and cartridge may cooperate to form an aerosol generating system which is a smoking system. The device may have a size comparable to a conventional cigar or cigarette. The cartridge may have a size comparable to a conventional cigar or cigarette. The smoking system may have a total length between approximately 30 mm and approximately 150 mm. The smoking system may have an external diameter between approximately 5 mm and approximately 30 mm.

Preferably, the aerosol generating system is an electrically operated smoking system.

According to the invention, there is also provided an aerosol generating system comprising a storage portion for storing liquid aerosol-forming substrate, the liquid storage portion having an internal passageway; a vaporizer for heating the liquid aerosol-forming substrate to form an aerosol, the vaporizer at least partially inside the internal passageway in the liquid storage portion; and a porous interface at least partially lining the internal passageway for conveying the liquid aerosol-forming substrate from the liquid storage portion towards the vaporizer.

In one embodiment, the container is prism-shaped having an annular cross section, the inner radius of the annulus is the radius of the internal passageway of the container, and the outer radius of the annulus defines the exterior of the container.

In that embodiment, the porous interface may comprise a hollow tube of porous material, the outer dimension of the hollow tube being substantially equal to the diameter of the internal passageway of the container.

Preferably, the aerosol generating device is electrically operated and the vaporizer comprises an electric heater for heating the liquid aerosol-forming substrate, the electric heater being connectable to an electric power supply in the aerosol generating device.

In that embodiment, the electric heater is preferably in contact with the porous interface.

In a preferred embodiment, the cartridge or the aerosol generating device or both the cartridge and the aerosol generating device comprise at least one air inlet; the cartridge or the aerosol generating device or both the cartridge and the aerosol generating device comprise at least one air outlet, and the air inlet and the air outlet are arranged, when the cartridge is in use with the aerosol generating device, to define an air flow route from the air inlet to the air outlet via the internal passageway of the container.

Features described in relation to one aspect of the invention may be applicable to another aspect of the invention.

The invention will be further described, by way of example only, with reference to the accompanying drawings, of which:

FIG. 1 shows a perspective view of an embodiment of a cartridge for use with an aerosol generating device according to the invention;

FIG. 2 shows a perspective exploded view of the cartridge of FIG. 1;

FIG. 3 shows a perspective view of a first embodiment of an internal heater for use with a cartridge according to the invention; and FIG. 4 shows a perspective view of a second embodiment of an internal heater for use with a cartridge according to the invention.

FIG. 1 is a perspective view of an embodiment of a cartridge for use with an aerosol generating device according to the invention. FIG. 2 is a perspective exploded view of the cartridge of FIG. 1. In FIGS. 1 and 2, the cartridge is for use with an electrically operated aerosol generating device having an electric power supply and electric circuitry.

Referring to FIGS. 1 and 2, the cartridge 100 comprises a storage portion in the form of a cylindrical container 101. Container 101 has a first end 101a, a second end 101b, and an outer housing 101c. Container 101 defines an internal passageway 103. Container 101 forms a reservoir for liquid aerosol-forming substrate between the outer housing 101*c* of the container and the internal passageway 103. Inside the internal passageway 103, there is provided a vaporizer (not visible in FIG. 1) in the form of internal heater 105 surrounded by a porous interface in the form of porous tube 107. The structure of the internal heater 105 will be described further with reference to FIGS. 3 and 4. In this embodiment, there is further provided a separation wall 109 between the porous tube 107 and container 101, closing part 111, and mouthpiece parts 113 and 115.

The cartridge 101 is arranged to be received in an aerosol generating device (not shown) including an electric power supply and electric circuitry. The aerosol generating device may further, although not necessarily, include a puff detection device. The electric circuitry and puff detection device may be programmable and may be used to manage the aerosol generating device operation. In this embodiment, the first end 101*a* of the container 101 is received closest to the electric power supply and electric circuitry in the aerosol generating device. The internal heater 105 is connected to the electric power supply and electric circuitry in the aerosol generating device. The second end 101*b* of the container 101 is received at the mouthpiece end of the aerosol generating device. The cartridge 100 or the aerosol generating device (not shown) or both the cartridge and the aerosol generating device may include an air inlet, an air outlet at the mouthpiece end, and an aerosol-forming chamber.

In use, operation is as follows. Liquid aerosol-forming substrate in the reservoir formed by container 101 is conveyed through the porous tube 107 towards the internal heater 105. When a user draws on the aerosol generating device at the mouthpiece end, ambient air is drawn through an air inlet in either the cartridge or the aerosol generating device and through the internal passageway 103 in the container 101. If the aerosol generating device includes a puff detection device, the puff detection device senses the puff and activates the internal heater 105. Otherwise, the internal heater 105 may be activated manually. The electric power supply in the aerosol generating device supplies electrical energy to the internal heater 105 to heat the liquid in the porous tube 107 adjacent the internal heater 105. The liquid in the porous tube 107 is vaporized by the internal heater 105 to create a supersaturated vapour in the internal passageway 103. At the same time, the liquid being vaporized is replaced by further liquid moving through the porous tube 107 from the reservoir. The supersaturated vapour created is mixed with and carried in the air flow from the air inlet through the internal passageway 103. The vapour condenses to form an inhalable aerosol, which is carried towards the air outlet and into the mouth of a user.

FIGS. 1 and 2 show one example of a cartridge for use with an aerosol generating device according to the present invention. Other examples are possible, however. The cartridge simply needs to include or receive a liquid aerosol-forming substrate and comprise a vaporizer located at least partially in the internal passageway of the container and separated from the liquid by a porous interface at least partially lining the internal passageway. For example, the vaporizer may not comprise a heater, in which case another device may be included to vaporize the liquid aerosol-forming substrate. For example, a puff detection device need not be provided. Instead, the device could operate by manual activation, for example the user operating a switch when a puff is taken. For example, the overall shape and size of the housing could be altered.

Preferably, the cartridge is disposable and is arranged to cooperate with an aerosol generating device which is reusable. The cartridge may be refilled or replaced when the liquid is used. Thus, when the liquid aerosol-forming substrate in the cartridge has been used up, the cartridge may be disposed of and replaced with a new cartridge, or the empty cartridge may be refilled. However, the aerosol generating device may not be designed to operate in conjunction with a separate cartridge. Instead, the aerosol generating device may include or receive a liquid aerosol-forming substrate in a storage portion and comprise a vaporizer located at least partially in the internal passageway of the liquid storage portion and separated from the liquid by a porous interface at least partially lining the internal passageway. That is to say, the aerosol generating device may comprise all the components described in relation to the cartridge. Additionally, the aerosol generating device may comprise an electric power supply and electric circuitry. Preferably, however, there is provided an aerosol generating device arranged to operate in conjunction with a cartridge. Preferably, the aerosol generating device is reusable and the cartridge is replaceable or refillable. Thus, when the liquid aerosol-forming substrate in the cartridge has been used up, the cartridge may be disposed of and replaced with a new cartridge, or the empty cartridge may be refilled.

The cartridge shown in FIGS. 1 and 2 has a relatively straightforward construction, which simplifies manufacture. The internal heater 105 is protected from damage by the container 101 and, because the internal heater 105 is contained within the internal passageway 103 of the container 101 (rather than downstream of the container as in prior art arrangements), the overall length of the cartridge, and hence the aerosol generating device, can be reduced. Moreover, the container 101 acts as an insulator thereby preventing the outside of the cartridge, and aerosol generating device, from overheating. Gravity may assist in conveying the liquid in the top part of the container 101 through the porous interface, and the chance of the porous interface drying out is reduced. As the supersaturated vapour condenses in the internal passageway 103 to form the aerosol, any aerosol droplets which accumulate in the internal passageway, may be absorbed by the porous interface. This enables the accumulating droplets to be reused, which reduced wastage.

The porous tube 107 can be made from a variety of porous materials and preferably has a known, pre-defined porosity. Examples include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. Porous tubes of different porosities can be used to accommodate different liquid suitable physical properties such as density, viscosity, surface tension and vapour pressure. The porous tube must be suitable so that the required amount of liquid can be delivered to the heater. In the embodiment shown in FIGS. 1 and 2, the porous tube extends along the length of the internal passageway. However, this need not be the case and the porous tube may extend only along part of the internal passageway. The dimensions of the porous tube can be chosen according to the desired operating characteristics of the aerosol generating device, for example, the amount of liquid aerosol-forming substrate desired to be vaporized.

FIG. 3 is a perspective view of a first embodiment of an internal heater 105 for use with a cartridge like that shown in FIGS. 1 and 2. Internal heater 105 comprises a first electrical connection portion 301 at a first end of the internal heater and a second electrical connection portion 305 at a second end of the internal heater. There is provided a first electrical connection blade 303 for electrically connecting the first electrical connection portion 301 to an electrical power supply and a second electrical connection blade 307 for electrically connecting the second electrical connection portion 305 to an electrical power supply. A heating filament in the form of heating coil 309 extends between the first electrical connection portion 301 and the second electrical connection portion 305.

In the embodiment of FIG. 3, the first 301 and second 305 electrical connection portions and the heating coil 309 are manufactured separately and are subsequently joined together, for example by welding. The first and second electrical connection portions are in the form of hollow tubes of electrically conducting material, although alternative shapes are possible. The heating coil 309 is in the form of a spiral of electrically resistive material, although alternative shapes are possible.

The cylindrical shape of the first 301 and second 305 electrical connection portions and the heating coil 309 define a cylindrical bore. When the heater is assembled, together with the porous tube, in the internal passageway of the container, an air flow route is defined through the cylindrical bore defined by the internal heater. The rigidity of the first 301 and second 305 electrical connection portions, in particular, assist in maintaining the shape of the internal passageway 103 and hence the air flow route through the aerosol generating device.

Preferably, the internal heater forms a snug fit inside the internal passageway 103 and porous tube 107. This prevents the internal heater and porous tube from falling out of the internal passageway, for example, when the aerosol generating device is shaken or inverted. In addition, preferably, the heating coil 309 is in contact with the porous tube when the heater and porous tube are assembled in the internal passageway of the container. This ensures a good transfer of heat to the liquid aerosol-forming substrate, which allows consistent formation of the aerosol. The length of the heating coil 309, and other dimensions of the internal heater 105, can be chosen as desired according to the required amount of heating.

FIG. 4 is a perspective view of a second embodiment of an internal heater 105' for use with a cartridge like that shown in FIGS. 1 and 2. Internal heater 105' comprises a first electrical connection portion 401, a second electrical connection portion 405 and an electrical joining portion 409. The electrical joining portion 409 is at a first end of the internal heater and the first electrical connection portion 401 is at a second end of the internal heater. The first electrical connection portion 401 is joined to the electrical joining portion 409 via an elongate portion 411. The second electrical connection portion 405 is at the second end of the internal heater adjacent the first electrical connection portion 401 and is connected to the electrical joining portion 409 via a heating filament 413. Heating filament 413 extends between the electrical joining portion 409 and the second electrical connection portion 405. There is also provided a first electrical connection blade 403 for electrically connecting the first electrical connection portion 401 to an electrical power supply and a second electrical connection blade 407 for electrically connecting the second electrical connection portion 405 to an electrical power supply.

In the embodiment of FIG. 4, the first 401 and second 405 electrical connection portions, the electrical joining portion 409 and the heating filament 413 are manufactured together from a single sheet of electrically resistive material. The sheet of electrically resistive material may have any suitable shape. The first 401 and second 405 electrical connection portions, the electrical joining portion 409 and the heating filament 413 may be cut from the sheet of electrically resistive material, for example, by a laser or by a chemical or electrical processor by high pressure water jet. Alternatively, the sheet of electrically resistive material may be pre-formed in the desired shape. Once the sheet has the appropriate shape, the sheet may be folded, rolled, curved or bent so as to form a cylindrical tube, as shown in FIG. 4.

When the cut sheet of electrically resistive material is rolled to form the heater, the cylindrical shape of the first 401 and second 405 electrical connection portions, the electrical joining portion 409 and the heating filament 413 define a cylindrical bore. When the heater is assembled, together with the porous tube, in the internal passageway of the container, an air flow route is defined through the cylindrical bore defined by the internal heater. The shape of the internal heater assists in maintaining the shape of the internal passageway 103 and hence the air flow route through the aerosol generating device.

Preferably, the internal heater forms a snug fit inside the internal passageway 103 and porous tube 107. This prevents the internal heater and porous tube from falling out of the internal passageway, for example, when the aerosol generating device is shaken or inverted. In addition, preferably, the heating filament 413 is in contact with the porous tube when the heater and porous tube are assembled in the internal passageway of the container. This ensures a good transfer of heat to the liquid aerosol-forming substrate, which allows consistent formation of the aerosol. In particular, the construction by rolling of the internal heater 105' may provide a spring or elastic effect, ensuring good contact between the heating filament 413 and the porous tube, when the heater and porous tube are assembled in the internal passageway. The length of the heating filament 413, and other dimensions of the internal heater 105, can be chosen as desired according to the required amount of heating.

In the embodiments of FIGS. 3 and 4, the air flow route is through the cylindrical bore defined by the internal heater. The air flows through the centre of the internal heater. That is to say, the size of the internal passageway and the internal heater defines the size of the air flow route. Thus, the internal passageway and cylindrical bore formed by the internal heater may act as an aerosol-forming chamber for assisting or facilitating generation of the aerosol. In addition, the size of the internal passageway and the internal heater may be used to assist with control of the aerosol. A small internal passageway and internal heater diameter may result in a high air flow rate through the aerosol generating device which may result in smaller droplets in the aerosol. A large internal passageway and internal heater diameter, on the other hand, may result in a low air flow rate through the aerosol generating device which may result in larger droplets. The droplet size in the aerosol may affect the user experience. The size of the internal passageway and internal heater is preferably pre-set according to the aerosol-forming substrate and the desired aerosol properties. Alternatively, however, the size of the internal passageway and internal heater may be variable by a user.

In one embodiment (not shown), there is provided a nozzle arranged to extend into the internal passageway of the container 101 when the cartridge is received in the aerosol generating device. The nozzle may form part of the aerosol generating device or part of the cartridge. The nozzle provides an air inlet into the internal passageway. If the internal heater defines a cylindrical bore which surrounds the air flow route, the nozzle may be arranged to extend into the cylindrical bore defined by the internal heater. The nozzle may allow the incoming air flow to be directed. For example, the nozzle may allow the incoming air flow to be directed directly onto the internal heater, directly onto the porous interface, across the surface of the internal heater, across the surface of the porous interface, or in any other desired direction. This may affect the aerosol formation which may, in turn affect the user experience. In addition, the nozzle may provide an air inlet or inlets having a small cross section, which will increase the air flow speed. This may also affect the aerosol formation by reducing the droplet size in the aerosol.

Thus, according to the invention, the aerosol generating device includes a storage portion having an internal passageway, a vaporizer at least partially contained in the internal passageway and a porous interface at least partially lining the internal passageway. This provides a number of advantages. Embodiments of the aerosol generating device have been described with reference to FIGS. 1 and 2, and embodiments of the vaporizer have been described with reference to FIGS. 3 and 4. Features described in relation to one embodiment may also be applicable to another embodiment.

The invention claimed is:

1. An aerosol generating device, comprising:
a storage portion configured to store an aerosol-forming substrate, the storage portion having an outer housing and an internal passageway, the storage portion forming a reservoir for the aerosol-forming substrate between the outer housing and the internal passageway;
a vaporizer configured to heat the aerosol-forming substrate to form an aerosol, the vaporizer at least partially inside the internal passageway in the storage portion; and
a porous interface at least partially lining the internal passageway configured to convey the aerosol-forming substrate from the storage portion towards the vaporizer,
wherein the aerosol generating device is electrically operated and the vaporizer comprises an electric heater configured to heat the aerosol-forming substrate, wherein the electric heater comprises:
a first electrical connection portion,
a second electrical connection portion, and
a heating filament between the first and the second electrical connection portions,
wherein the first electrical connection portion is a first cylindrical electrical connection portion, the second electrical connection portion is a second cylindrical electrical connection portion, and the heating filament is a cylindrical heating element, and
wherein the cylindrical shape of the first and the second electrical connection portions and the heating filament define a cylindrical bore, wherein an air flow route is defined through the cylindrical bore.

2. The aerosol generating device according to claim 1, wherein the first and the second electrical connection portions are in a form of hollow tubes.

3. The aerosol generating device according to claim 2, wherein the first electrical connection portion is located at a first end of the internal passageway, the second electrical connection portion is located at a second end of the internal passageway, and the heating filament has a first end joined to the first electrical connection portion and a second end joined to the second electrical connection portion.

4. The aerosol generating device according to claim 2, wherein the hollow tubes are hollow tubes of electrically conducting material.

5. The aerosol generating device according to claim 1, wherein the heating filament is in contact with the porous interface.

6. The aerosol generating device according to claim 1, wherein the electric heater further comprises a sheet of electrically resistive material shaped to form the first electrical connection portion, the second electrical connection portion, and the heating filament.

7. The aerosol generating device according to claim 6, wherein the electric heater further comprises a cylindrical electrical joining portion, and wherein the cylindrical shape of the first and the second electrical connection portions, the cylindrical electrical joining portion, and the heating filament define the cylindrical bore.

8. The aerosol generating device according to claim 1, wherein the porous interface comprises a hollow tube of porous material, an outer dimension of the hollow tube being substantially equal to a diameter of the internal passageway of the storage portion.

9. The aerosol generating device according to claim 1, further comprising at least one air inlet and at least one air outlet, the at least one air inlet and the at least one air outlet being arranged so as to define an air flow route from the at least one air inlet to the at least one air outlet via the internal passageway of the storage portion.

10. A cartridge, comprising:
a storage portion configured to store an aerosol-forming substrate, the storage portion having an outer housing and an internal passageway, the storage portion forming a reservoir for the aerosol-forming substrate between the outer housing and the internal passageway;
a vaporizer configured to heat the aerosol-forming substrate to form an aerosol, the vaporizer at least partially inside the internal passageway in the storage portion; and
a porous interface at least partially lining the internal passageway configured to convey the aerosol-forming substrate from the storage portion towards the vaporizer,
wherein the vaporizer comprises an electric heater configured to heat the aerosol-forming substrate, wherein the electric heater comprises:
a first electrical connection portion,
a second electrical connection portion, and
a heating filament between the first and the second electrical connection portions,
wherein the first electrical connection portion is a first cylindrical electrical connection portion, the second electrical connection portion is a second cylindrical electrical connection portion, and the heating filament is a cylindrical heating element, and
wherein the cylindrical shape of the first and second electrical connection portions and the heating filament define a cylindrical bore, wherein an air flow route is defined through the cylindrical bore.

11. The cartridge according to claim 10, wherein the first and the second electrical connection portions are in the form of hollow tubes.

12. The cartridge according to claim 11, wherein the first electrical connection portion is located at a first end of the internal passageway, the second electrical connection portion is located at a second end of the internal passageway, and the heating filament has a first end joined to the first electrical connection portion and a second end joined to the second electrical connection portion.

13. The cartridge according to claim 11, wherein the hollow tubes are hollow tubes of electrically conducting material.

14. The cartridge according to claim 10, wherein the heating filament is in contact with the porous interface.

15. The cartridge according to claim 10, wherein the electric heater further comprises a sheet of electrically resistive material shaped to form the first electrical connection portion, the second electrical connection portion, and the heating filament.

16. The cartridge according to claim 15, wherein the electric heater further comprises a cylindrical electrical joining portion, and wherein the cylindrical shape of the first and the second electrical connection portions, the cylindrical electrical joining portion, and the heating filament define the cylindrical bore.

17. The cartridge according to claim 10, wherein the porous interface comprises a hollow tube of porous material, an outer dimension of the hollow tube being substantially equal to a diameter of the internal passageway of the storage portion.

18. The cartridge according to claim 10, further comprising at least one air inlet and at least one air outlet, the at least one air inlet and the at least one air outlet being arranged so as to define an air flow route from the at least one air inlet to the at least one air outlet via the internal passageway of the storage portion.

19. An aerosol generating system, comprising:
a cartridge and an aerosol generating device, the cartridge or the aerosol generating device comprising
a storage portion configured to store an aerosol-forming substrate, the storage portion having an outer housing and an internal passageway, the storage portion forming a reservoir for the aerosol-forming substrate between the outer housing and the internal passageway;
a vaporizer configured to heat the aerosol-forming substrate to form an aerosol, the vaporizer at least partially inside the internal passageway in the storage portion; and
a porous interface at least partially lining the internal passageway configured to convey the aerosol-forming substrate from the storage portion towards the vaporizer,
wherein the aerosol generating device is electrically operated and the vaporizer comprises an electric heater configured to heat the aerosol-forming substrate,
wherein the electric heater comprises:
a first electrical connection portion,
a second electrical connection portion, and
a heating filament between the first and the second electrical connection portions,
wherein the first electrical connection portion is a first cylindrical electrical connection portion, the second electrical connection portion is a second cylindrical electrical connection portion, and the heating filament is a cylindrical heating element,
wherein the cylindrical shape of the first and the second electrical connection portions and the heating filament define a cylindrical bore, and wherein an air flow route is defined through the cylindrical bore.

* * * * *